(12) United States Patent
Muller

(10) Patent No.: US 6,280,189 B1
(45) Date of Patent: Aug. 28, 2001

(54) CLIP HOLDER FOR DENTAL MATERIAL

(75) Inventor: Frank Muller, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 09/465,564

(22) Filed: Dec. 17, 1999

Related U.S. Application Data

(60) Provisional application No. 60/121,759, filed on Feb. 26, 1999.

(30) Foreign Application Priority Data

Jan. 26, 1999 (DE) .................................. 199 03 019

(51) Int. Cl.⁷ ...................................................... A61C 3/00
(52) U.S. Cl. ............................. 433/49; 433/163; 224/217
(58) Field of Search ........................ 433/49, 163; 224/217

(56) References Cited

U.S. PATENT DOCUMENTS

| | | | |
|---|---|---|---|
| 1,545,452 | * 7/1925 | Pinn ...................................... | 433/163 |
| 5,368,482 | 11/1994 | Johnsen et al. ...................... | 433/163 |
| 5,732,862 | * 3/1998 | Bull ...................................... | 433/163 |
| 6,036,490 | * 3/2000 | Johnsen et al. ...................... | 433/163 |

FOREIGN PATENT DOCUMENTS 0 302 004  2/1989 (EP) .

* cited by examiner

*Primary Examiner*—John J. Wilson
(74) *Attorney, Agent, or Firm*—John C. Thompson; Alan S. Koiman

(57) ABSTRACT

A clip holder has a base body and an elastic securing clip connected to the base body for securing the clip holder to a body part of the user by elastic stress. The base body has at least one cutout for receiving a dental material unit, preferably containing a single dose of dental material.

14 Claims, 1 Drawing Sheet

CLIP HOLDER FOR DENTAL MATERIAL

This application claims benefit to Provisional Application No. 60/121,759 filed Feb. 20, 1999.

BACKGROUND OF THE INVENTION

The present invention relates to a clip holder for dental material that is to be placed onto a body part and comprises a securing clip that is especially placed onto the finger of a user where it is held under elastic stress. It at least partially surrounds the finger or body part The clip holder has a base body to which the securing clip is connected.

Such a clip holder is known from U.S. Pat. No. 5,368,482. This known clip holder has a substantially conical securing device that receives a sponge for cleaning soiled areas resulting during treatment with dental materials. In addition, the securing tongue supports a semicircular securing wire. A prophylactic paste can be introduced into this holding wire for treatment of the patient.

This solution is, in principle, well suited when the dentist needs a certain paste for a particular patient The dental treatment requires, however, often further substances so that the receiving depression according to the aforementioned U.S. patent would have to be exchanged in order to thus allow use of further substances.

On the other hand, the flat metal strip that serves as a receiving element for the dental material, will not suppress vibrations so that there is the risk that the user, i.e., the treating dentist, will lose portions of the dental material placed into the depression. This is undesirable especially because of the resulting soiling.

Furthermore, it has been suggested to provide finger clips with small depressions which can be filled with different dental materials. Filling is done with dental material from bulk containers, and the dentist can remove in sequence the needed substances and place them into the depression, or, in the alterative, a plurality of finger clips are used, for example, a total of three which are then filled with different types of dental materials. A disadvantage is that the dental materials that are provided in bulk can be contaminated by the utensils that are used for filling the depressions when, for example, accidentally the utensil of one material is introduced into a different kind of bulk material. Furthermore, there is a risk that the dental materials can be confused especially when the dentist does not employ the same arrangement for the respective finger clips.

A disadvantage of the known holders is also that the received dental materials are not supported sufficiently well. This is especially relevant because the support action at one finger by its very nature does not allow for a steady containment so that it would be impossible to use liquid dental materials with such finger clips.

It is therefore an object of the present invention to provide a clip holder of the aforementioned kind which is especially suitable to receive dental materials in an impact-reduced and contamination-protected manner, even with single dose units, and provides ergonomic handling.

SUMMARY OF THE INVENTION

The present invention is characterized in that the base body of the clip holder has a cutout for prepared dental material units.

With the inventive clip holder it is first especially advantageous that the prepared dental material units can be simply inserted without risking that already during insertion soiling will occur. The design of the cutouts as part of the base body will eliminate an unsteady connection such as provided by a sheet metal strip (prior art) so that, even when a lateral impact occurs, the resulting vibrations are received and compensated by the base body and the finger or body part to which this clip holder is secured, but are not introduced into the dental material unit. The cutout provides a protective action and surrounds practically a securing collar of the dental material unit so that it preferably retreats in a lateral direction.

An especially favorable feature is the design of the dental material unit as an elongate capsule. Because of the elongate, downwardly extending capsule design it is possible to use liquid dental materials. It is preferred to limit the degree of filling to a maximum of 75% of the height of the dental material unit.

For example, the dental material unit can be a capsule-like tube having a height of 2 cm and an outer diameter of 5 mm. Removal of the liquid is then carried out in a manner known to a person skilled in the art by a small brush or a similar handling tool. A dental material contained in such a capsule, in general, has sufficient surface tension in order to prevent leakage from the capsule, for example, when the inner diameter of the capsule is 3 or 4 mm. In any case, the narrow and deep design of the dental material unit results in a container that prevents accidental spillage and this is true also for dental materials in the form of fine powders.

Especially fine powders have the tendency to whirl up so that the surrounding air and thus the dental practice are exposed to soiling and contamination.

These contaminations can be avoided in an especially favorable manner in that the dental material unit is safely supported. According to an advantageous embodiment, the dental material unit is laterally secured with elastic stress at the finger or the securing clip. When the securing dip is placed onto the finger the dental material unit is laterally pushed away so that it is, on the one hand, securely clamped in the cutout but, on the other hand, can be easily removed from the cutout when the clip holder is removed from the finger.

In an especially preferred embodiment, two dental material units are arranged adjacent to one another. The two dental material units thus have fixed positions, but allow a safe and vibration-protected receiving action with the aforementioned advantages. A color coating of the respective capsule-like tubes can avoid confusion of the dental materials with great reliability. It is especially advantageous in this context that the two dental material units extend in the direction of the axis of the body part so that they are not projecting too much and are thus indirectly supported by the body part.

Even though the inventive dip holder is primarily intended as a finger clip, it is understood that according to other embodiments it is also possible to use such clip holders on the wrist. This is, for example, disclosed in European Patent Application 0 302 004.

It is especially advantageous that the base body and the securing clip, including the cutouts, is produced as a unitary molded plastic part. With this solution it can be ensured that no pointed inner comers will result which are prone to soiling. With a suitable selection of materials, the clip holder can be sterilized and/or disinfected in a suitable manner or can be autoclaved. Furthermore, an especially secure and steady receiving action for the dental material units will result. The plastic part can, for example, be produced as unitary part by injection molding.

The connection between the cutout and the dental material unit can be embodied in any suitable manner. While a plug-in connection which provides the required clamping action by lateral spreading, is especially beneficial with regard to manipulation, it is understood that, if desired, also other suitable fastening measures may be realized. For example, the dental material unit can be provided with an adhesive so that it can be glued into place but removed when needed from the cutout. Furthermore, it can be threaded into the cutout whereby a coarse thread is preferred that can be easily cleaned. Finally, a catch or snap connection between the cutout and the dental material unit can be provided. Furthermore, it is not required that the cutout completely surrounds the dental material unit. A supporting action that ensures that upon lateral impact the dental material unit will not become detached from the cutout is sufficient whereby, however, a circular (annular) support action is preferred.

According to another preferred embodiment, the dental material unit has a securing collar having a diameter that is greater than the inner diameter of the cutout so that the dental material unit projects only by the height of the securing collar from the base body of the clip holder. Inventively, it is especially favorable that the design of the inventive clip holder provides for positioning of the dental materials close to the body. The dental material units extend practically L-shaped at two tangents of the body part, especially the finger, and are thus guided thereat. This results in an excellent supporting action but especially also in a protective action with regard to impact since the projecting length relative to the finger is reduced to a minimum.

It is understood that the inventive design is not limited to the realization of two dental material units in respective cutouts at the base body. For example, it is possible to provide a plurality of cutouts serially arranged, i.e., extending parallel to the longitudinal axis of the body part. It is also possible to arrange cutouts on both sides of the finger or other body part so that the dental materials surround the finger in a U-shaped arrangement. In this embodiment, the securing dip is preferably not laterally (radially) slipped onto the finger but is pushed axially onto the finger and is preferably of an annular design. It is understood that the used term securing clip is not limited to open securing clips. Instead the chosen term securing clip is meant to include any type of securing element that is capable of being supported on a body part.

BRIEF DESCRIPTION OF THE DRAWING

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1–4.

Figure 1:
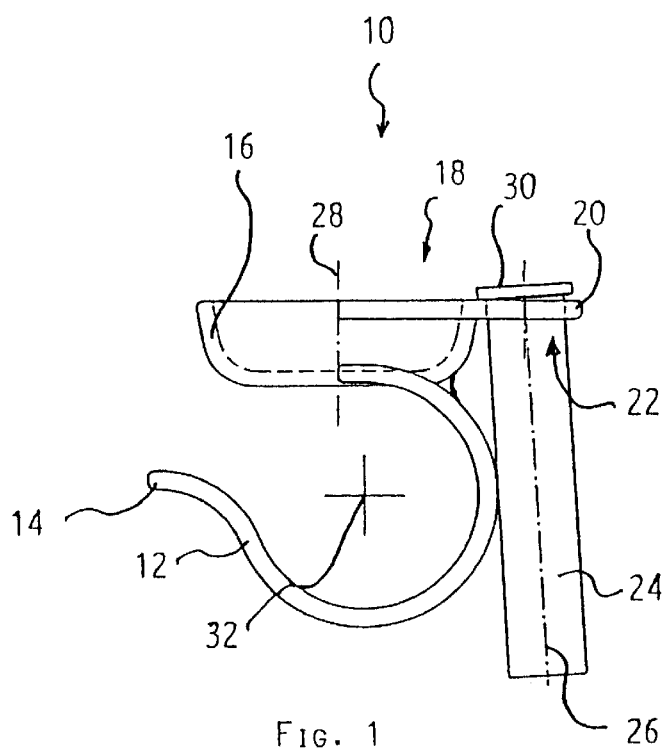
FIG. 1 shows a side view of the clip holder.

The clip holder 10 represented in FIG. 1 has an elastic securing clip 12 which is substantially embodied as a ¾ circular arc, i.e., extends over an angular range of approximately 270°. Its free end is bent outwardly with a spreading tongue 14 while the other end is connected to the base body 16 so as to form a unitary part thereof.

The base body 16 has a depression 18 which is suitable for receiving dental materials. The depression 18 is relatively flat and extends across the entire width of the securing clip 12. The base body 16 furthermore has a flat flange 20 with two cutouts 22 which are embodied for receiving the dental material units 24.

The dental material units 24 have an axis 26 which in the represented position is at a slant to the axis 28 of the depression 18. They are pushed away from the finger by the securing clip 12 and are thus slightly canted within the cutout 22. This canting action improves support and securing of the dental material units whereby the canting action is further improved by placing the securing clip 12 onto the finger so that further spreading of the securing clip pushes the dental material units 24 farther away.

Even without the spreading action the securing collar 30 prevents that the dental material unit 24 can fall out of the cutout 22.

Preferably, the inner diameter of the cutout 22 is slightly greater than the outer diameter of the dental material unit 24 but smaller than the diameter of the securing collar 30.

Figure 2:
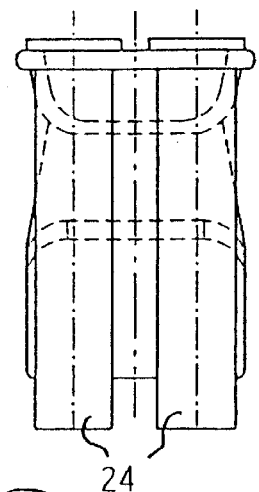
FIG. 2 shows the embodiment according to FIG. 1 in an end view.
Figure 3:
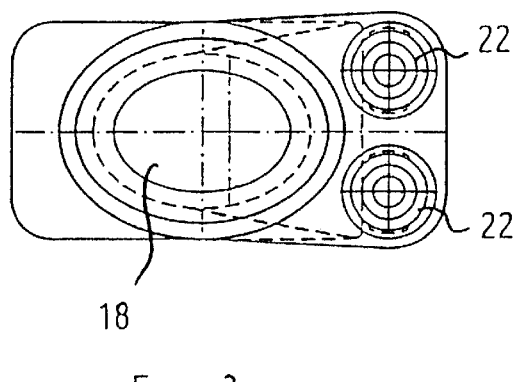
FIG. 3 shows a plan view of the embodiment according to FIG. 1.

FIG. 2 illustrates that preferably two dental material units 24 are positioned adjacent to one another in the direction of the axis 32 of the body part, especially a finger. Both dental material units 24 rest at the securing clip 12 whereby according to a modified embodiment it is suggested that each dental material unit 24 rests directly at the finger. FIG. 3 shows that the depression 18 is substantially oval. It is matched substantially in its width and length to the size of the inventive clip holder 10 so that, on the one hand, only a minimal projection is provided and, on the other hand, the required surface area and volume for receiving dental materials is realized which is needed for practical applications. For example, a paste or a similar material can be placed into this depression which is not prone to spillage.

Figure 4:
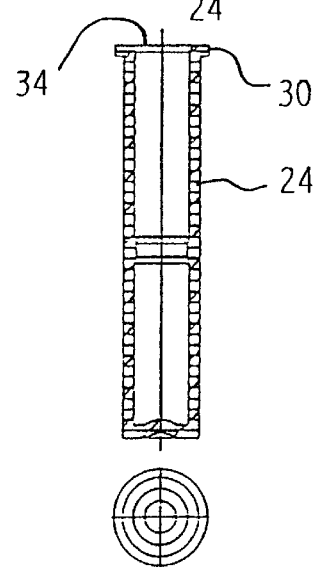
FIG. 4 shows a dental material unit for use in the inventive clip holder, partly in a sectioned and partly in a plan view.

FIG. 4 shows how the dental material unit 24 can be embodied as a capsule or a tube. Preferably, a prepared (portioned) single dose unit. i.e., an amount required for one dental application, is provided which can be optionally filled with a liquid dental material. The tall and narrow design of the dental material unit 24 allows receiving of the dental material, even a liquid, without the risk of spillage whereby the cohesion of the liquid prevents that, even when sudden movements are performed, the dental material will spill from the unit 24. Preferably, the filling level of the dental material unit 24, especially when liquids are used, is limited to, for example, 2⁄3 of the total height of the dental material unit 24.

According to a preferred embodiment it is suggested to cover the dental material unit 24 with a protective foil at its upper end. The protective foil can extend across the securing collar 30 and can be fused thereto. Upon use of the dental material unit 24, the protective foil 34 is removed whereby the removal can be performed after the dental material unit 24 has been inserted into the cutout 22, but it is also possible to remove the foil 34 beforehand.

What is claimed is:

1. A clip holder (10) comprising:
a base body (16) having at least one cutout (22);
an elastic securing clip (12) connected to said base body (12) for securing said clip holder (10) on a body part of a user by elastic stress; and
an elongated dental material receiving unit (24) received within said cutout, the unit extending generally perpendicularly of the body part and being positioned laterally of the elastic securing clip, said receiving unit being pushed by said elastic securing clip (12) to improve support and securing of the elongated dental material receiving unit.

2. A clip holder (10) according to claim 1, wherein said base body (16) has an oval depression (18) for receiving dental materials, wherein the longer axis of said oval depression (18) extends in a direction of said longitudinal axis, wherein said depression (18) has a bottom to which said elastic securing clip (12) is fastened.

3. A dip holder (10) according to claim 1, wherein said elastic securing clip (12) has a width matching substantially a width of said base body in a direction perpendicular to said longitudinal axis.

4. A clip holder (10) according to claim 1, wherein said elongated dental material receiving unit (24) is secured in said cutout (22) against accidental removal.

5. A clip holder (10) according to claim 4, wherein said elongated dental material receiving unit (24) has a catch for securely engaging said cutout (22).

6. A clip holder (10) according to claim 1, wherein said elongated dental material receiving unit (24) has a cylindrical shape and wherein said cutout (22) is circular, wherein an inner diameter of said cutout (22) an outer diameter of said elongated dental material receiving unit (24) match one another such that said elongated dental material receiving unit (24) is secured by press fit in said cutout (22).

7. A clip holder (10) according to claim 1, wherein said elongated dental material receiving unit (24) is secured by screwing in said cutout (22).

8. A clip holder (10) according to claim 1, wherein said elongated dental material receiving unit (24) is secured by a snap connection in said cutout (22).

9. A clip holder (10) according to claim 1, wherein said elongated dental material receiving unit (24) is secured by a releasable adhesive connection in said cutout (22).

10. A clip holder (10) according to claim 1 embodied free of inner comers that are difficult to disinfect.

11. A clip holder (10) according to claim 1, wherein said elastic securing dip (12) is a ¾ circular arc having a first end connected to said base body (16).

12. A clip holder (10) according to claim 11, wherein said elastic securing clip (12) and said base body (16) are a unitary part.

13. A clip holder (10) according to claim 11, wherein said elastic securing clip (12) has a second end forming a tongue (14) bent outwardly relative to said circular arc in order to facilitate insertion of the body part into said elastic securing clip (12).

14. A clip holder according to claim 1, wherein said elongated dental material receiving unit (24) is laterally stressed when said elastic securing clip (12) is positioned on the body part.

* * * * *